(12) United States Patent
Pulkkinen et al.

(45) Date of Patent: Mar. 26, 2019
(10) Patent No.: US 10,238,915 B2

(54) METHOD TO DETERMINE BODY'S PHYSIOLOGICAL RESPONSE TO PHYSICAL EXERCISE FOR ASSESSING READINESS AND TO PROVIDE FEEDBACK, AND SYSTEM FOR IMPLEMENTING THE METHOD

(71) Applicant: Firstbeat Technologies Oy, Jyväskylä (FI)

(72) Inventors: Aki Pulkkinen, Jyväskylä (FI); Sami Saalasti, Jyväskylä (FI); Kaisa Hämäläinen, Jyväskylä (FI)

(73) Assignee: Firstbeat Technologies Oy, Jyväskylä (FI)

( * ) Notice: Subject to any disclaimer, the term of this patent is extended or adjusted under 35 U.S.C. 154(b) by 294 days.

(21) Appl. No.: 14/912,242

(22) PCT Filed: Sep. 10, 2014

(86) PCT No.: PCT/FI2014/050689
§ 371 (c)(1),
(2) Date: Feb. 16, 2016

(87) PCT Pub. No.: WO2015/036651
PCT Pub. Date: Mar. 19, 2015

(65) Prior Publication Data
US 2016/0184637 A1 Jun. 30, 2016

(30) Foreign Application Priority Data
Sep. 11, 2013 (FI) .................................. 20135918

(51) Int. Cl.
*A63B 24/00* (2006.01)
*A61B 5/024* (2006.01)
(Continued)

(52) U.S. Cl.
CPC .......... *A63B 24/0062* (2013.01); *A61B 5/024* (2013.01); *A61B 5/11* (2013.01);
(Continued)

(58) Field of Classification Search
CPC ... A61B 5/002; A61B 5/024; A61B 5/11; A61B 5/222; A61B 5/486; A61B 5/741;
(Continued)

(56) References Cited

U.S. PATENT DOCUMENTS

2006/0032315 A1* 2/2006 Saalastic ............... A61B 5/222
73/808
2006/0063980 A1* 3/2006 Hwang ................ A61B 5/222
600/300

(Continued)

FOREIGN PATENT DOCUMENTS

WO 2012140322 A1 10/2012

OTHER PUBLICATIONS

International Search Report dated Jan. 15, 2015 from corresponding International Patent Application No. PCT/FI2014/050689; 4 pgs.
(Continued)

*Primary Examiner* — Michael Carey
(74) *Attorney, Agent, or Firm* — Maier & Maier, PLLC

(57) ABSTRACT

The invention relates to a method and a system for determining body's readiness to respond to physical exercise and for providing feedback to a user. In the method the user starts to perform an exercise, an earlier performance level is determined before starting a performance check having steps of: an instant performance level of the user is determined, the earlier performance level is compared to the instant performance level, a readiness index is determined according to the said comparison and optionally with background and/or training history of the user, a feedback is given according to the determined readiness index.

19 Claims, 13 Drawing Sheets

Figure 1:
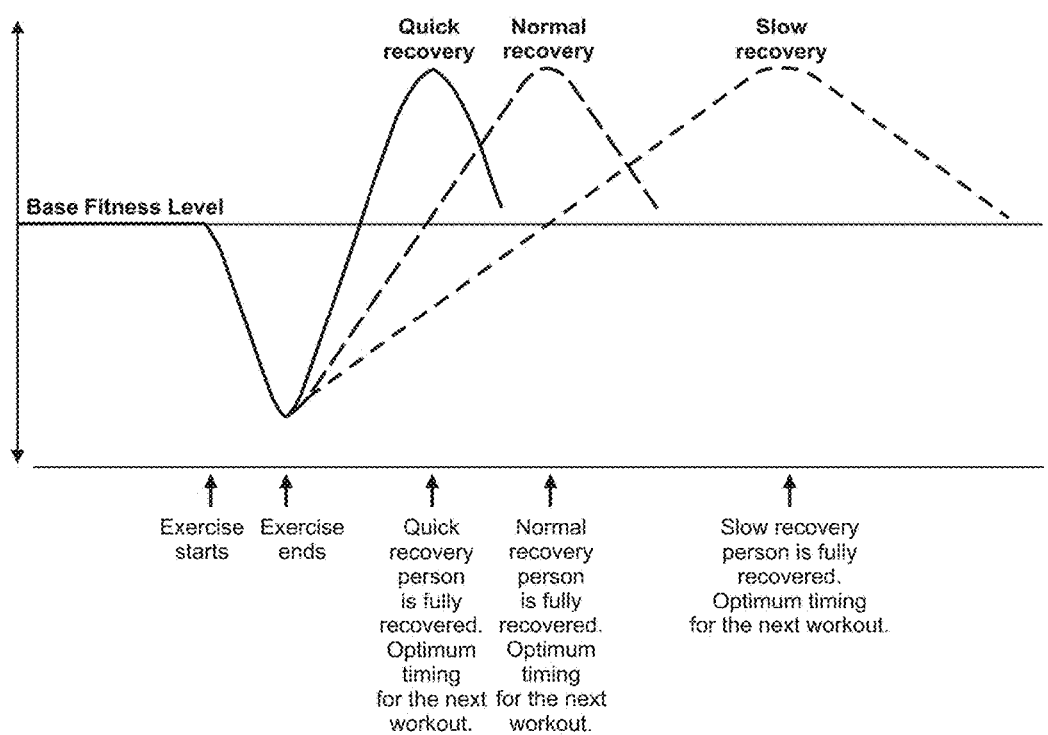

(51) Int. Cl.
*A61B 5/22* (2006.01)
*G06F 19/00* (2018.01)
*A61B 5/11* (2006.01)
*A61B 5/00* (2006.01)

(52) U.S. Cl.
CPC .............. *A61B 5/222* (2013.01); *A61B 5/486* (2013.01); *G06F 19/00* (2013.01); *G06F 19/3481* (2013.01); *A61B 5/002* (2013.01); *A61B 5/741* (2013.01); *A61B 2503/10* (2013.01); *A63B 2024/0068* (2013.01)

(58) Field of Classification Search
CPC ............ A61B 2503/10; A63B 24/0062; A63B 2024/0068; G06F 19/3481
USPC .................................................. 600/300, 301
See application file for complete search history.

(56) References Cited

U.S. PATENT DOCUMENTS

| | | | |
|---|---|---|---|
| 2011/0152695 A1 | 6/2011 | Granqvist et al. | |
| 2011/0263993 A1 | 10/2011 | Martikka et al. | |
| 2013/0172764 A1* | 7/2013 | Buckley | A61B 5/0205 600/509 |
| 2013/0190903 A1* | 7/2013 | Balakrishnan | A61B 5/7246 700/91 |

OTHER PUBLICATIONS

International Preliminary Report on Patentability dated Nov. 24, 2015 from corresponding International Patent Application No. PCT/FI2014/050689; 10 pgs.

* cited by examiner

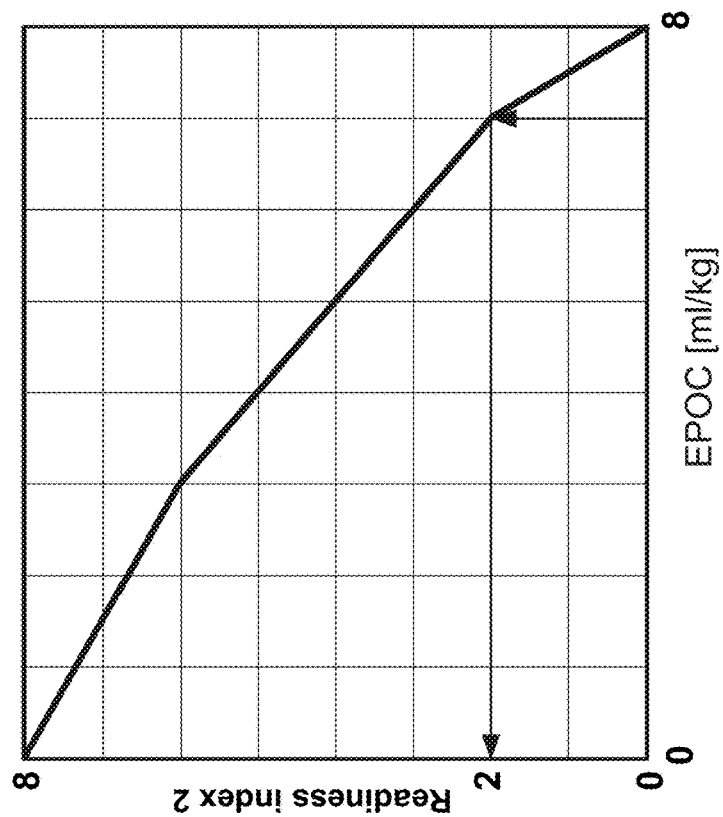
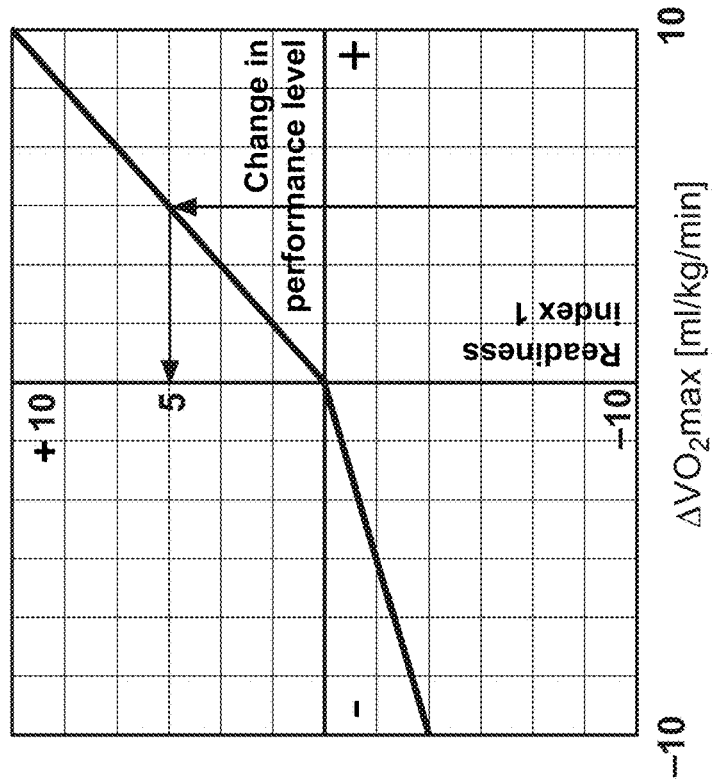
Fig. 5a
Fig. 5b

| Recovery time left Before Exercise | Instant performance level | Readiness to exercise |
|---|---|---|
| Green | ↑ | Green |
| Green | ↔ | Green |
| Green | ↓ | Yellow |
| Yellow | ↑ | Green |
| Yellow | ↔ | Yellow |
| Yellow | ↓ | Red |
| Red | ↑ | Yellow |
| Red | ↔ | Red |
| Red | ↓ | Red |

| Sunday 17.3 at 12:00 | Before workout | At warm-up: | Result |
|---|---|---|---|
| Training effect | – | 1.5 | 4.5 "Highly Improving" |
| Recovery time | 0h "Full recovery" GREEN | 1h "Go for it" GREEN | 48h "Ease a bit" RED |
| Vo2max | 46 ml/kg/min "GOOD" | – | 46 ml/kg/min "GOOD" |

| Monday 18.3 at 13:00 | Before workout | At warm-up: | Result |
|---|---|---|---|
| Training effect | – | 1.5 | 3.5 "Improving" |
| Recovery time | 24h "Almost there" YELLOW | 1h "Go for it" GREEN | 24h "Almost there" YELLOW |
| Vo2max | 46 ml/kg/min "GOOD" | – | 48 ml/kg/min "GOOD" |

Fig. 10

| Recovery time | User communication (example) | Suggested next workout |
|---|---|---|
| Green 0-18 h | Go for it! Complete or close to complete recovery. Ready to train (hard) again. | > 3.5 Highly improving workout |
| Yellow 18-36 h | Almost there! You may still continue improving training. | < 3.5 Improving workout |
| Orange 36-54 h | Ease up a bit! Maintaining basic endurance workouts and rest recommended. Good fitness improvement expected after recovered. | < 2.9 Maintaining basic endurance workout |
| Red 54-72 h+ | Time to take a break! Rest and easy training recommended to allow your body to recover. Very good fitness boost expected after recovery. | < 2.0 Easy workouts to recover |

Fig. 11

METHOD TO DETERMINE BODY'S PHYSIOLOGICAL RESPONSE TO PHYSICAL EXERCISE FOR ASSESSING READINESS AND TO PROVIDE FEEDBACK, AND SYSTEM FOR IMPLEMENTING THE METHOD

The invention relates to an improved method and system for determining body's readiness to respond to physical exercise and provide feedback, wherein
 physiological response is measured
 external workload is measured or entered
 instant performance level of the user is determined
 feedback is given during and/or after exercise.

The method could be implemented in any device comprising a processor, memory and software stored therein and an user interface, e.g. heart rate monitor, fitness device, mobile phone, PDA device, wristop computer or personal computer.

BACKGROUND OF THE INVENTION

High training load and recovery plays an important role in training, particularly in athletic training. There has to be a balance between hard and easy training and rest both within a single training week and within longer training periods. Finding a balance between training load and recovery is a key factor in improving fitness.

Periodization is important in training. Usually athletes have several very hard training periods each year, during which both the intensity and volume of training are very high. These kinds of overreaching periods are very exhaustive but necessary for athletes to further improve their performance. However, performance can improve only if hard training is followed by adequate recovery.

Supercompensation is very incremental improvement of performance level. The results are usually shown over time and multiple training sessions. Every training session is not intended to bring supercompensation. A large part of aerobic endurance training is low intensity long duration training that prepares the capabilities of the body for harder training.

The timing of supercompensation and the recovery needs is individual and it will greatly be affected of the acute situations, such as training, stress, eating and sleeping. The real recovery is unknown until the recovery has taken place. The best and the only indisputable measure of recovery time is the change of performance. FIG. 1 shows an example of different kinds of recovery time from the same workout: quick-recovery, normal recovery and slowly recovery. Because the recovery from workout can be very different in different person and even with same person in different situations and depending on time of day, it is very important to determine the body's readiness to exercise during each exercise session.

The prior art has documented some work on the measurement of exercise workload and recovery. Nissila et al. (US 2011021319A1) have presented an apparatus for metabolic training load, mechanical stimulus, and recovery time calculation. This method's recovery time assessment is based on the measured training load/workload from the whole exercise. The method does not assess user's performance level and therefore does not provide information on the capacity of the user to perform the exercise. Furthermore, as the method is based on analysis of the workload of the whole exercise, the method can provide information only after the exercise, and the method fails to make assessment of recovery time or body's readiness to exercise during exercise. Thus, as the method does not make an assessment of the readiness of the user to do the exercise during the exercise, the method is not capable of calibrating and providing feedback already during the exercise. Saalasti et al. (U.S. Pat. No. 7,192,401 B2) have presented a method for monitoring accumulated body fatigue for determining recovery during exercise or activity. This method provides recovery information already during exercise, but does not determine person's performance level and thereby does not calibrate the recovery time. The method is not also able to provide feedback to person's readiness to exercise.

Prior art has documented work on deriving information on the accumulation of body fatigue and exhaustion due to physical workload. Bernard et al. (U.S. Pat. No. 4,883,063) have presented a method for monitoring heat stress, as especially occurring in a hot factory environment. The solution includes an assessment of recovery on the basis of heart rate measurement, during which the person has to stay at rest for few minutes. The estimation of the recovery is somewhat problematic in the described method, since it requires few minutes of rest and is not therefore applicable to continuous monitoring of recovery within dynamic changes in exercise phases and intensities. In general, the method does not involve a differential estimation of the recovery component which impairs the estimation of the recovery during dynamic exercise.

SUMMARY OF THE PRESENT INVENTION

The invention aims is to estimate daily physiological response to exercise for assessing readiness and recovery, and to provide feedback in order to optimize training. The present invention aims also to avoid the drawbacks of the known methods and systems relating to estimate daily physiological response to exercise. It is intended to provide an improved method and system for assessing readiness and recovery, and providing feedback in order to optimize training. The characteristic features of the method according to the invention are stated in the accompanying claim 1 and the features of the system implementing the method are stated in claim 17. The method according to the invention helps in finding a balance between training load and recovery and improves feedback regarding to a body response. The method determines body's readiness to respond to physical exercise and provides feedback to a user, who has an earlier performance level. In the method
 the user starts to perform the exercise, wherein measuring of the intensity begins
 an earlier performance level is determined before a performance check having steps of
 an instant performance level of the user is determined by a relation of exercise intensity and determined external workout, the exercise intensity being determined by measured heart rate,
 an instant performance level of the user is determined by a relation of measured exercise intensity and determined external workload,
 the earlier performance level is compared to the instant performance level,
 a readiness index is determined according to the said comparison and optionally with background information and/or training history of the user,
 feedback is given according to the determined readiness index.

The determining of the performance level should be understood here widely. It may refer to any body response of a physical exercise, which body response indicates a change of the readiness or recovery time. Preferably it refers to the cardiorespiratory performance level, the relative heart rate being more than 50%. Some background information giving maxHR directly or indirectly is necessary if the absolute performance level (VO2max) should be determined. However, the evaluation could be carried also relatively just comparing any later result to previous one, eg. to the first value.

Also training history is needed in such extent that the recovery state could be registered. However, it is possible start an exercise and generate all necessary parameters for the exercise for determining the Readiness index.

The instant performance level is determined during any exercise and compared to an earlier performance level.

In another embodiment the recovery time is determined according to the determined readiness index. Readiness index is determined after the started and fully performed exercise or preferably during said started exercise, particularly readiness index is determined frequently. The readiness index is determined mainly by said comparison and optionally with background information and/or training history of the user.

In another embodiment the user is advised by the feedback at least with one of the following options:
  to continue training normally (e.g. green colour) if the determined readiness index indicates an improved performance level or being in a previous level,
  to maintain training intensity (yellow) if the determined readiness index seems not being full recovered or exhausted,
  to ease up training (red) if the determined readiness index indicates a decreased performance level. This feature helps exerciser's to choose the right exercise to the current time and optimize the performance level development.

In another embodiment user is advised by arrows to increase, maintain or decrease exercise load or intensity. In another embodiment user is advised by voice guiding.

Preferably the user is advised by the feedback regarding to an aim of the exercise and/or the user is advised by the feedback to choose an exercise type from a preset group of different exercise types. The user is may be advised with a development of the instant performance level. This feature helps user to exercise according to the goal by following only the acute effects of exercise to performance level. For example, if the aim of the exercise is to do easy/recovering workout, the device guide to lighten the load, if the performance level of the user is decreasing. Similarly, the hard exercise drops acutely performance level and intent to exercise like this, the device guides user to a suitable load.

In a preferable method a reliability of a value of the instant performance level is detected and each value with a low reliability is automatically excluded. This allows for reliable performance level assessment. For example running in the forest which is much heavier than the road, performance level assessment does not drop down.

Preferable exercise modality is detected. This means that the method detects e.g. cycling from running workloads (FIG. 4b.). This helps to determine reliable readiness index because the relationship between physiological response and external workload depends on the exercise modality.

The method is implemented by a system having CPU and memory and software therein.

In another embodiment background data of the user is adapted by feedback. This allows for more individualized feedback and training offered by changes in the performance level does not require to update manually to the device.

The instant performance level is determined preferably by the relation between a physiological response and an external workload during the exercise.

In another embodiment the start of the performing the exercise is detected automatically. Thus, it may be convenient that it is not necessary to start the procedure manually.

The invention and its embodiments are described more in detail with reference to following drawings, which present background and preferable embodiments of the invention.

Figure 2:
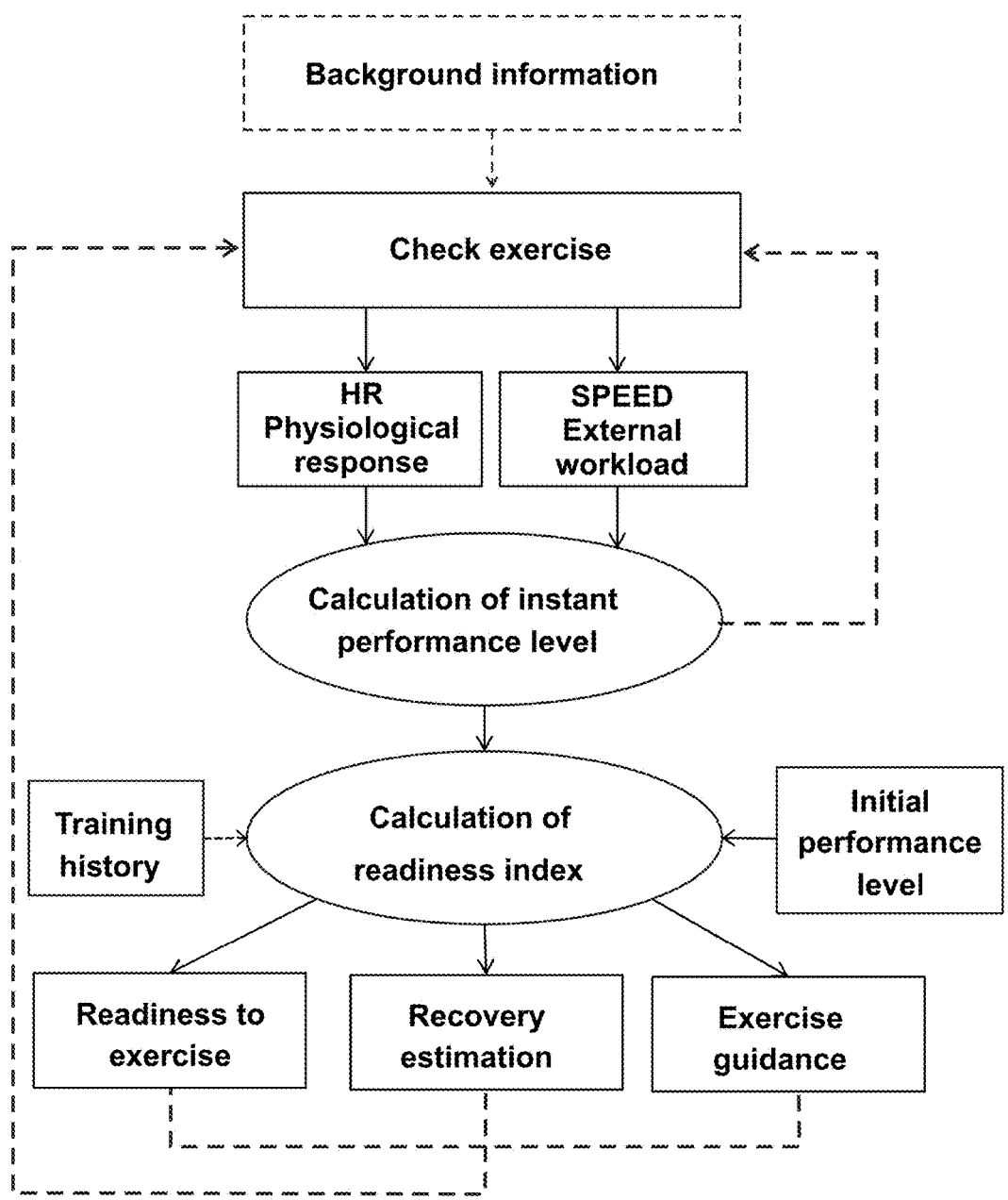
Figure 3:
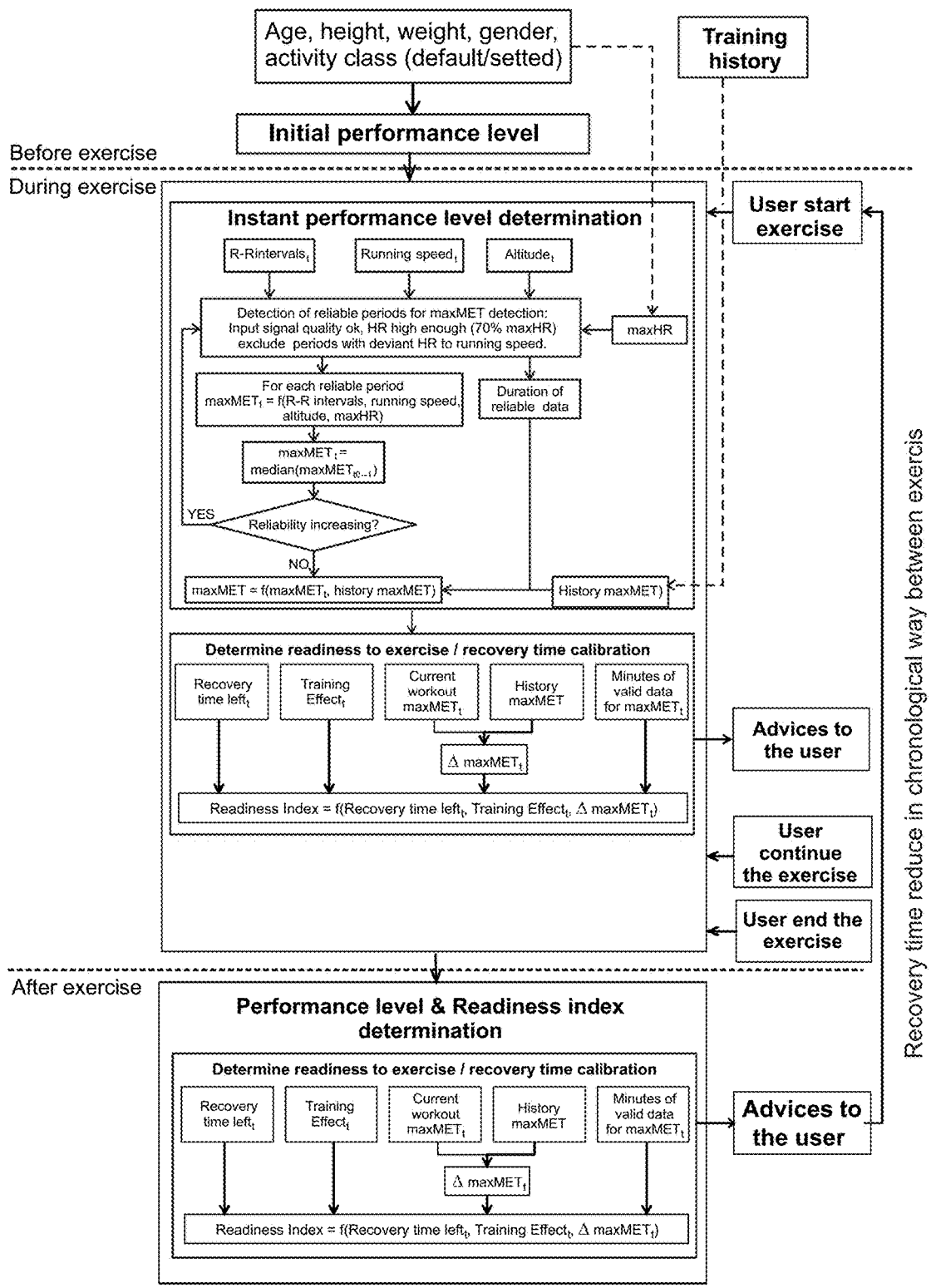
Figure 4A:
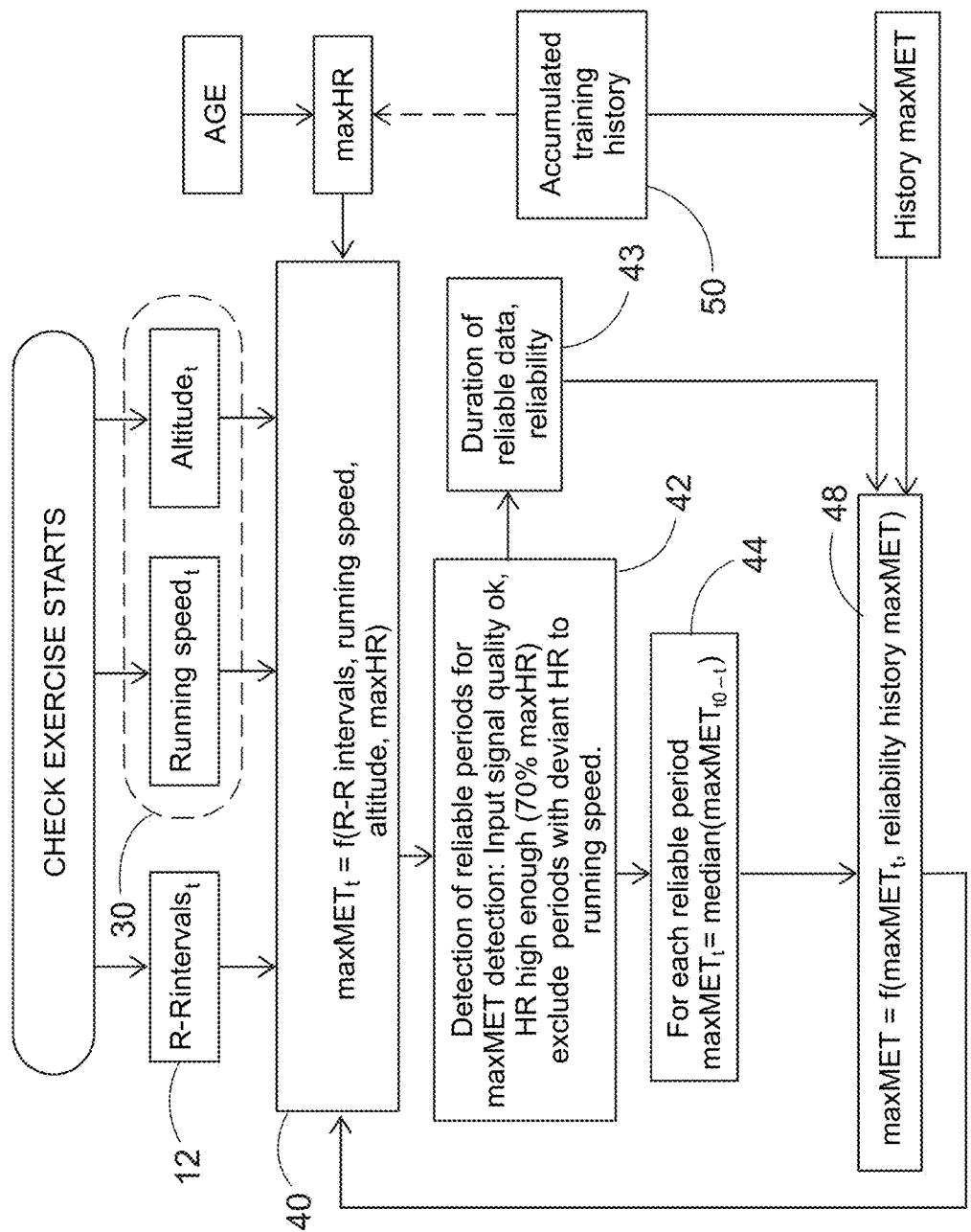
Figure 4B:
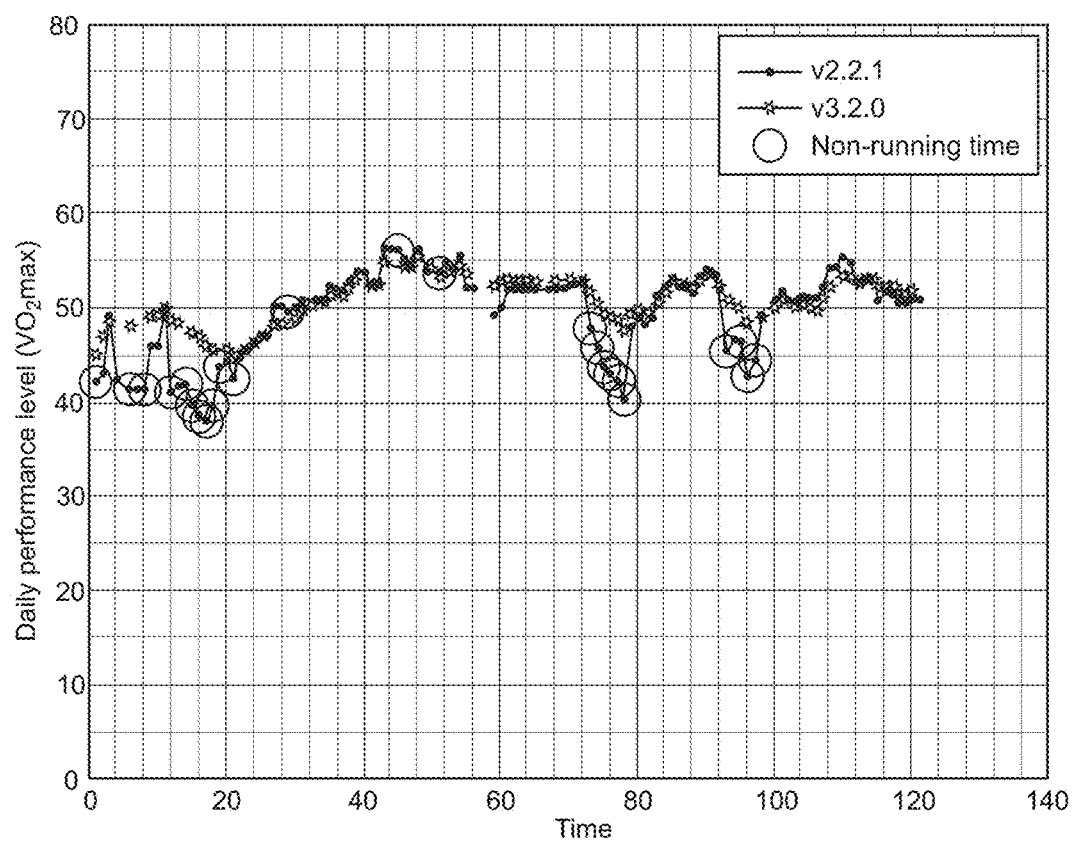

FIG. 1 presents a typical variation in recovery after the same workout of one individual in different times FIG. 2 presents the main logic of the method according to the invention FIG. 3 presents the flowchart of the recovery advisor according to a preferred embodiment FIG. 4a presents the flowchart for the assessment of an instant performance level FIG. 4b presents an example of automatic running workouts inclusion and other workouts exclusion FIG. 5a shows the relationship between change in performance level and readiness index. FIG. 5b shows the relationship between current workout's physiological load and readiness index.

Figures 6, 7:
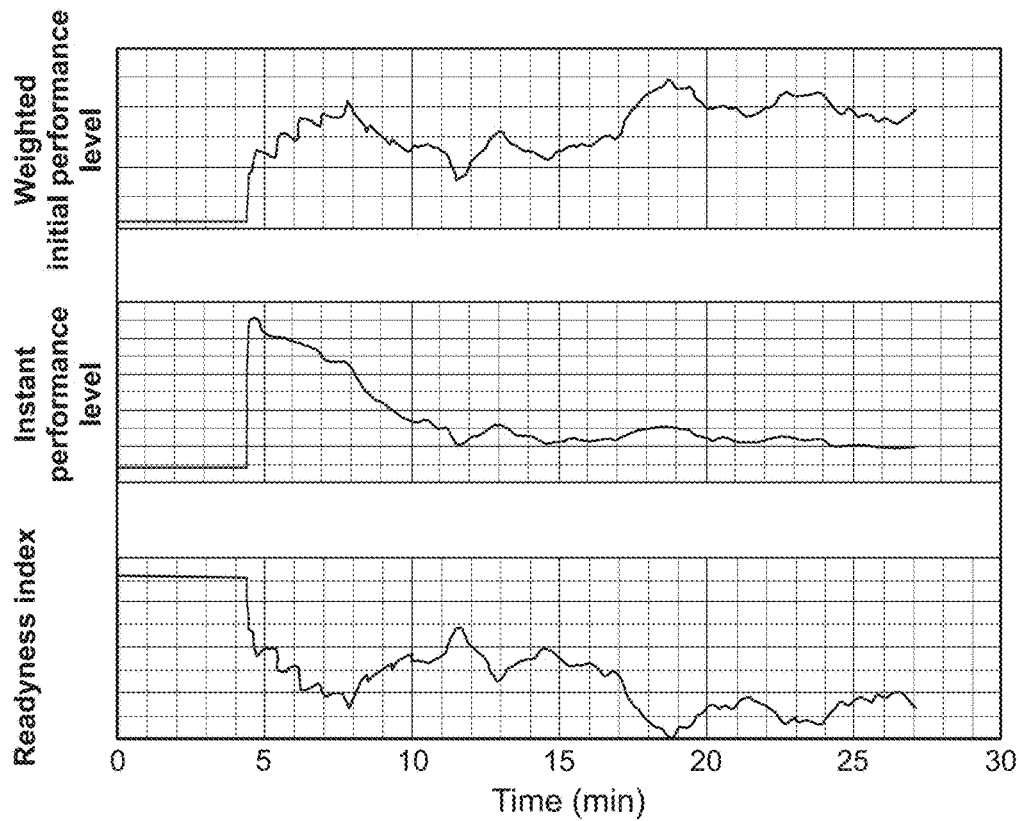

FIG. 6 presents an example of the recovery time accumulation according to the change in performance level.

FIG. 7 presents readiness to exercise in different kind of initial situations.

Figure 8:
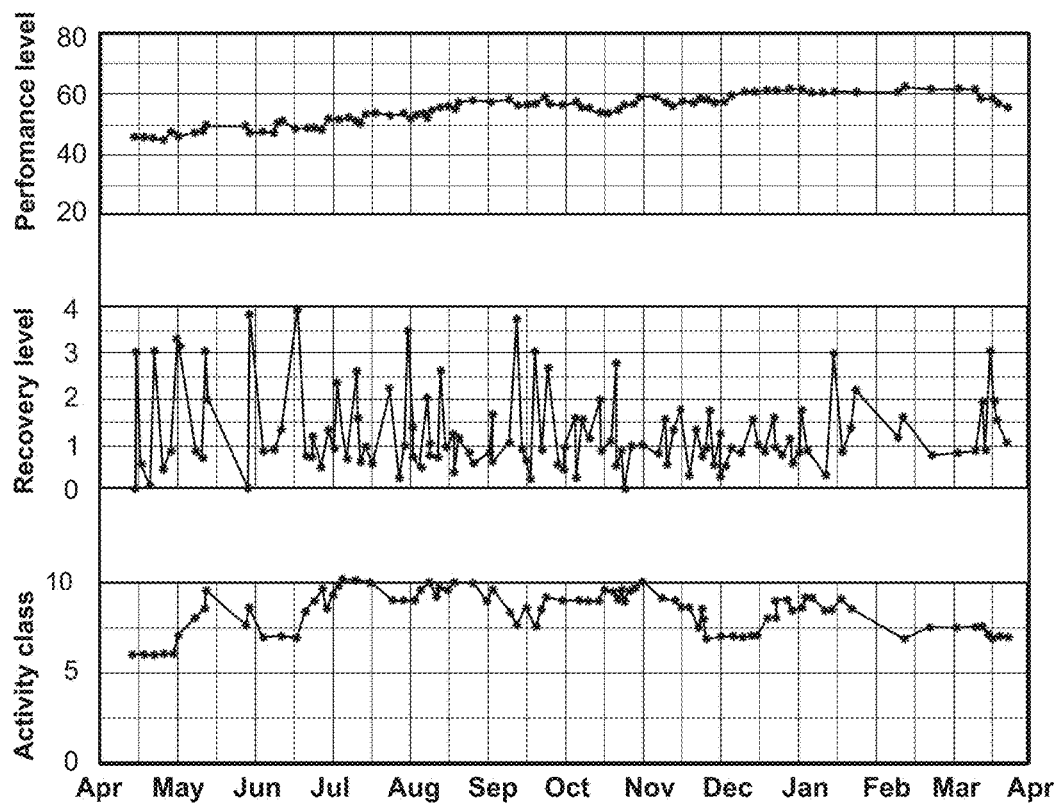

FIG. 8 presents an example of automatic personalization in one year view and recovery time adaptation according to performance level development.

Figure 9:
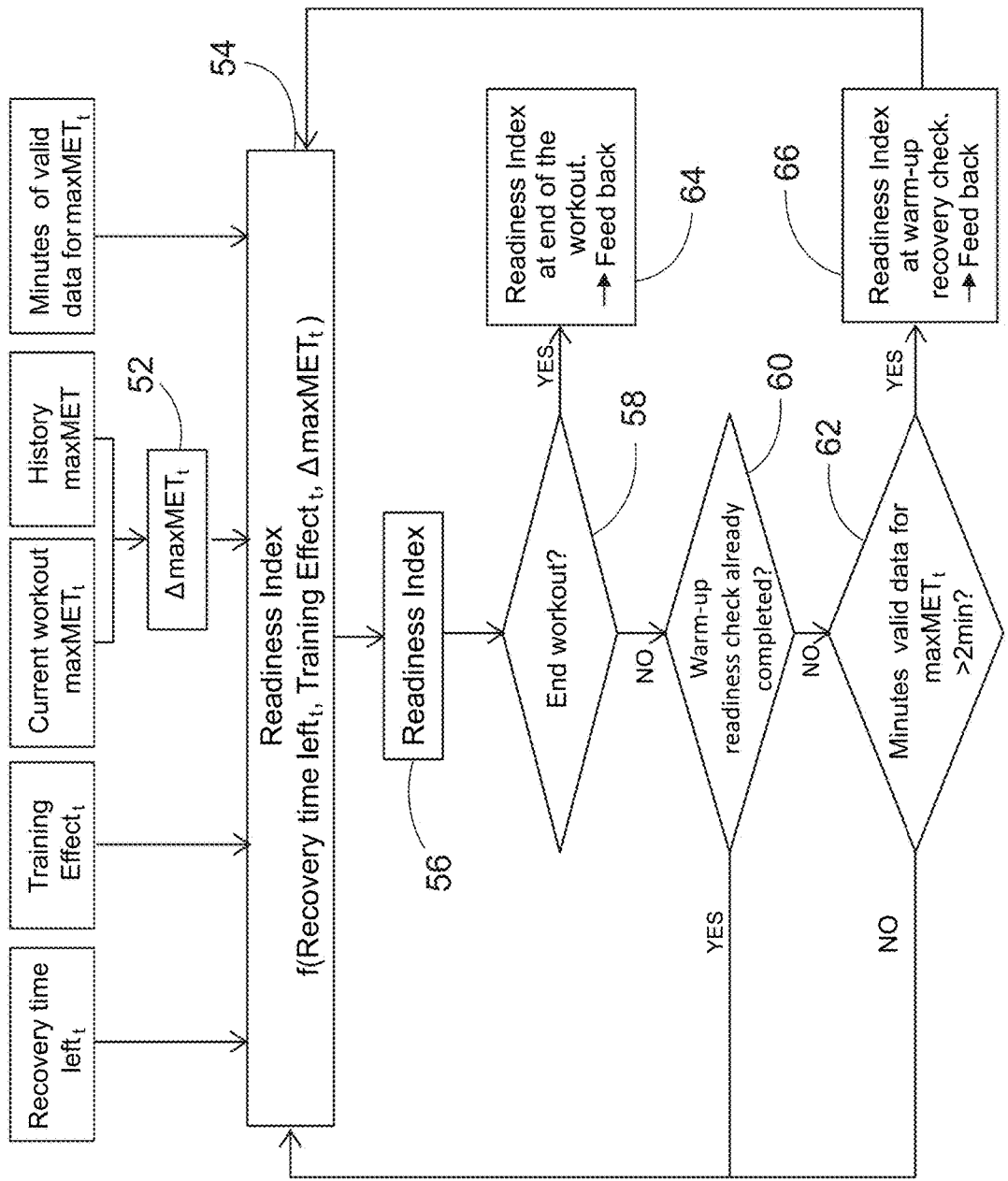

FIG. 9 presents the flowchart for the assessment of recovery time during or after exercise FIG. 10 presents another implement of recovery advisor in a wristop FIG. 11 presents an example of training advisor's feedback.

Figure 12:
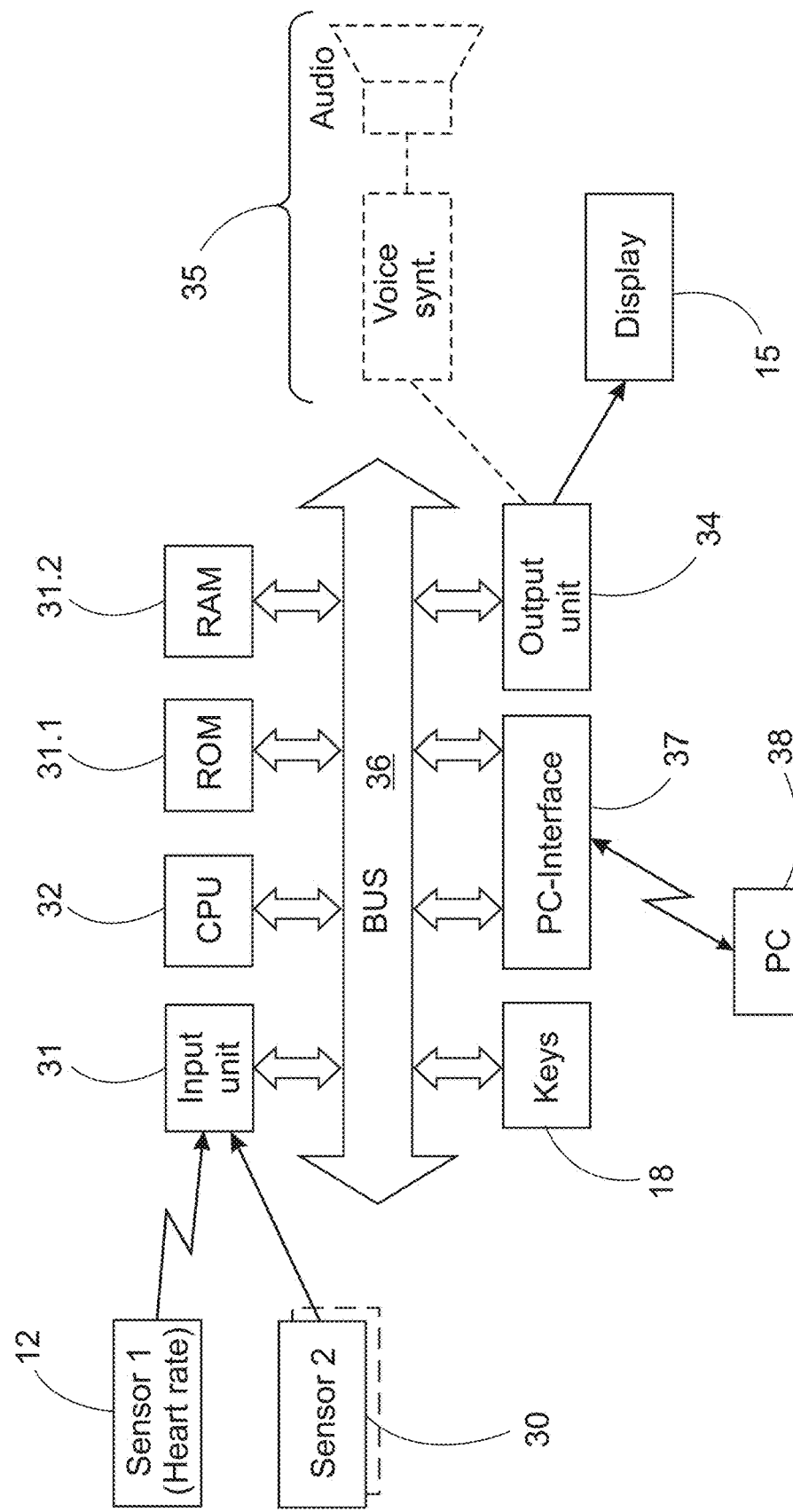

FIG. 12 presents a block diagram of the system with additional interfaces.

Figure 13A:
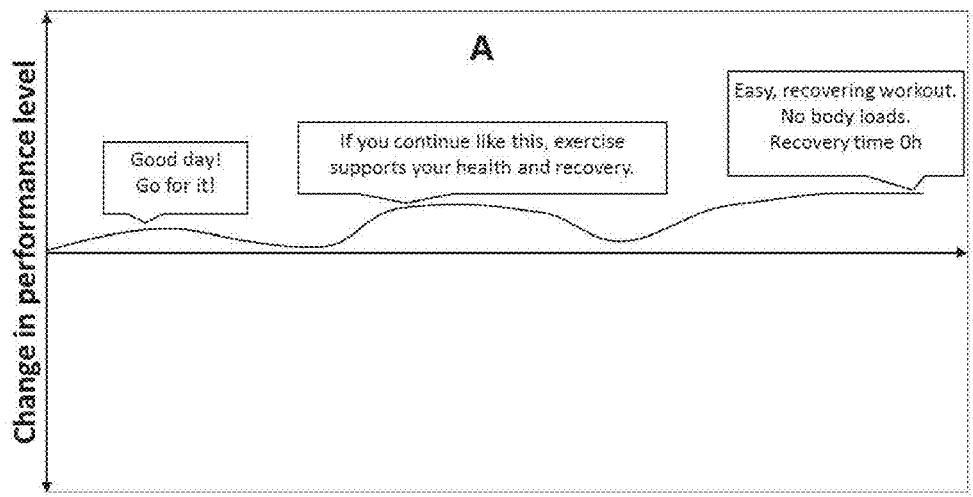
Figure 13B:
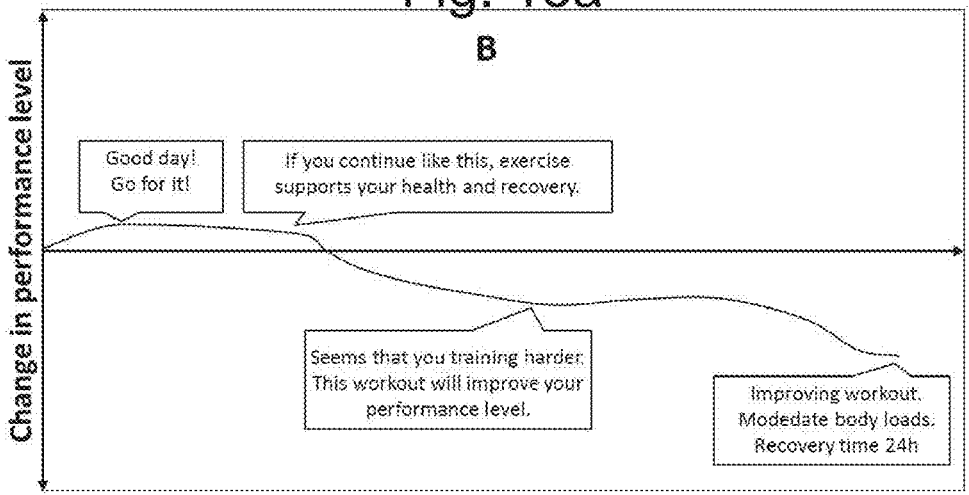
Figure 13C:
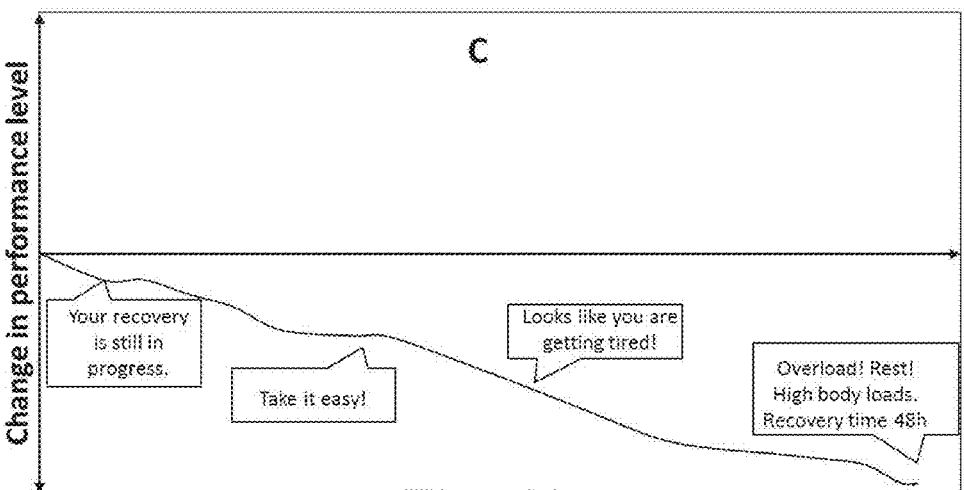

FIGS. 13a, 13b and 13c present guiding of exercise with different situations.

DETAILED DESCRIPTION OF THE INVENTION

Definitions of the Terms

Background Information
  Person's background information includes such as age, weight, height and gender and maximum HR. It refers to ability to perform physical exercise. 'Activity class' belongs to the same group. Some background information may be initially assumptions on which the device starts to edit according the data. The required background information depends on what kind of feedback the person will be given. A relative comparison could be carried totally without background information. The absolute performance level in a scale of VO2max requires background information. The background information may include also a target which can be a longer-term target or goal of the workout. The long-term goal may be a target time for a specific marathon, weight management or improving performance level. The workout target can be for example recovering workout or high intensity workout or a specific exercise.
Exercise
  Exercise can be any kind of physical activity. The device can automatically detect physical activity and therefore not need a separate start command. It should note that the user's ordinary exercise may have different parts:
a starting part of exercise providing the 'earlier performance level'
a continuation of exercise for a performance check The earlier exercise may be needed in order to determine personal data and training history, particularly activity class, and an earlier performance level. The term 'a exercise regarding determining body's readiness' refers to an exercise where calculation of readiness index is available and possible.

Physiological Response

Body's internal reaction to the external workload is heart rate (HR), oxygen consumption, energy expenditure or respiration rate or other measured value which determines body's response to external load. The heart rate (HR) is the most preferable variable to get the internal response, because heart rate is easily available and it is accurate to depict the exercise intensity. The maximum value of HR is determined often easily by empirical way; HRmax=(210−0.65*AGE). The default value is then adapted according to exercises.

External Workload

The external work rate. External workload data can be for example speed and altitude data from GPS or accelerometer, pedaling power or other data created by workload causing energy expenditure. The external workload can be measured or manually inputted such as distance or workload index.

Instant Performance Level

The person's current performance level, preferably as $VO2max$ (=3.5×METmax), which is determined according to relationship between physiological response and external workload. The performance level can be presented also with index value.

Earlier Performance Level

The person's performance level such as VO2max or METmax which is determined according to relationship between physiological response and external workload during exercise or estimated on the basis of the background information or inputted manually. Earlier performance level may be initially assumptions on which the device starts to edit according the data. Earlier performance level can be determined from current exercise's past time or from a previous exercise. Results are generally more accurate if the performance level of the previous exercise is known. In other hand the method is flexible if previous data is not necessary. Performance level can be presented also with index value.

Training History

Includes all information about training in the past: the training information before the start of the current workout and the current workout before instant performance level assessment. Training history can include for example information about how much recovery time has left from last workout, current workout training load such as Training effect or TRIMP etc.

Readiness Index

An index value which represent body's readiness for workout. High readiness index represents that body is ready to new workout because of body is recovered and has energy to exercise. Low readiness index represents that body is unrecovered. Readiness index can be determined in different ways:
1) relationship between instant and earlier performance levels
2) relationship between instant and earlier performance levels and combining the personal information.
3) relationship between instant and earlier performance levels and combining the information about training history.
4)) relationship between instant and earlier performance levels and combining the personal and training history information.

Readiness index is used to given different kinds of feedback to the user. This is also used for selection of next workout modality and intensity. For example if readiness index is low, exercise feedback guides to an easy exercise to avoid overloading.

Readiness to Exercise

How ready the body is for a new exercise. Readiness information can be given to the user numerically, verbally or visually.

Recovery Estimate

How long time is recommended to recover before next exercise to optimize training. Recovery information can be given to the user during or after exercise numerically, verbally or visually.

Exercise Feedback

Exercise feedback can include the feedback of the ongoing or next workout. The feedback may include model, time, duration and/or intensity of exercise etc. The feedback may also include feedback about the workout in relation to the target. The feedback can be given to the user during or after exercise numerically, verbally or visually e.g. by arrows.

Preferred Embodiments

FIG. 2 show the main logic of the method, where the body's readiness to physical exercise, wherein
earlier performance level and training history are known before an exercise
physiological response (heart rate) is measured and external workload is determined
instant performance level of the user is determined by the relation of them
earlier performance level is compared to instant performance level
training history is combined to the change of performance level as a result a variety of applications and feedback such as body's readiness to exercise, recovery time and exercise feedback during and after exercise.

An example of a flowchart for implementing the claimed method is shown in FIG. 3.
An earlier performance level is determined before the starting the exercise regarding determining body's readiness (performance check),
The user starts to perform the exercise;
The instant performance level of the user is determined by a relation of measured exercise intensity and determined external workload earlier performance level is compared to the instant performance level.
A readiness index is determined according to the said comparison and optionally with background and/or history data of the user,
A feedback is given according to the determined readiness index
Exercise end
Repeat the steps 3-6
Recovery time reduces in a chronological way between exercises
1) Instant Performance Level Assessment Maximal oxygen consumption ($VO_2max$) is defined as the maximal rate of oxygen intake during exhaustive exercise and denotes person's ultimate capacity for aerobic energy production. Usually this is achieved by stepwise exercise protocol to a voluntary exhaustion (maximal exercise stress test), during which the oxygen uptake is measured. Also non-exercise methods are available to estimate person's VO2max based on individual characteristics such as, for example, age. sex, anthropometric information, history of physical activity, or resting level physiological measurements (e.g. Jackson et al. 1990). Assessment of performance level is more accurate when background data is available.

This invention introduces a method for accurate assessment of person's instant performance level during any use performed exercise session. Preferably performance level evaluation is based on the well-known connection between the heart rate and power output (for example running speed or pedaling power). See FIG. 4. More information Seppanen et al (WO2009/133248A1) and Saalasti et al (WO2012140322A1).

The assessment of the instant performance level used in FIG. 3 is shown in more detailed in FIG. 4.

If cycling power is not known running exercise is automatically detected according heart rate and speed data, e.g., cycling workload gets none or low reliability VO2max. See FIG. 4b how the methods automatically exclude non running exercises (circles). VO2max estimation is stopped also for workout when reliability decreases for example due to HR drift in long duration workouts. Referring to FIG. 4a presenting the software implementation. After start internal and external exercise workout are read continuously. R-R-intervals are measured by heart rate sensor 12. External workout is obtained by one or more sensors 30 (Here Running speed & altitude). MaxHR is read from input data (eg. 210-0.65× 'age'). MaxMET (=VO2max/3.5) is calculated by an empirical equation $$maxMET=maxMET(HR, maxHR, \text{external exercise workout}).$$

Thus, instant performance level depicted by VO2max, can be predicted by relative heart rate and external workload.

The external exercise workload is measured by sensors 30, detecting running speed and altitude. The monitoring of the latter gives the grade (inclination) needed in the equation. Thus, the equation has been modified here: maxMET=maxMET(HR, maxHR, speed, grade) calculated periodically by the module 40. The coefficients $C_1$, $C_2$ and $C_3$ are determined using empirical data.

$$VO2max_i=(C_1-HR/maxHR)*C_2*(Speed+C_3)*(1+Grade)$$

The lower the heart rate, the better the user's performance level. Whenever the modality of the exercise is determined, the formula of performance level is adapted according to the determined modality (like running, cycling, rowing and walking).

While input values are read periodically by the sensors 12, 30, their quality is checked by preset criteria. The periods are typically 5 seconds, more generally in range 3-30 s. There are a set filter for each input value like HR should be at least 70% HRmax and speed below 7 m/s. However, the most useful criterion here sets a range for each calculated VO2max-value, like 20 ml/kg/min<$VO2max$<90 ml/kg/min This criterion sets a decent relation between heart rate and the external work out. The module 44 calculates a median value from reliable maxMET-values. The maxMET-value is calculated in the module 48 by the values of 'instant maxMET', 'history maxMET' and reliability. The 'history maxMET' has always minimum 60% weight. The 'instant maxMET' has weight of 0-40% depending on reliability. If input values or calculated maxMET value is out of range or there are less than preset minimum number, eg. 20 accepted points, the reliability is 0%. The reliability is calculated in module 43. After the minimum number of points has been reached the reliability starts to increase from zero depending on how many accepted points has been detected. The reliability reaches full 100%, when there are accepted values of matMEX$_t$ for 30 minutes.

Continuously updated accumulated training history data 50 gives History maxMET-value. In an example 'History maxMet' is 50, 'instant maxMet' is 45 and the duration of reliable data 5 minutes yield maxMET 49. If the duration is 25 minutes, the maxMET would be 46.

It can be estimated that there should be at least 10 minutes of free exercise or at least 2 minutes of guided exercise, when the first reliable results appear.

FIG. 4a does not contain an exit-module, when the exercise ends.

After the instant performance level is detected the result can be used to provide a variety of applications, feedback and guidance to the user.

2) Calculating Readiness Index

Readiness to exercise is determined according to comparison between person's earlier performance level and instant performance level. Comparison is the main factor in the calculation of Readiness index. The instant performance level is determined preferable automatically with free fitness test from the data which includes heart rate and work rate data. For reliable results, VO2max (=3.5×maxMET) is updated as reliability weighted average between the latest new workout value and history value. For updated VO2max, latest workout VO2max estimate may have weight of 0-40%.

Also on-going workout may effect on readiness index. The power output can be described for example with Training effect value which refers to training-induced development of performance level and performance. To determine the training effect of a single exercise, peak EPOC achieved during exercise and the activity class of an individual must be known. EPOC (excess post-exercise oxygen consumption) measures the quantity of exercise-induced disturbance of body's homeostasis. The activity class value represents the activity level of the previous month. Read more Saalasti et al. (U.S. Pat. No. 7,192,401 B2) Method for monitoring accumulated body fatigue for determining recovery during exercise or activity. In addition to information of changes in performance level and on-going workout intensity, the recovery time from last exercise can be taken account.

The readiness to exercise is calculated as FIGS. 5a and 5b. FIG. 5a shows the relationship between changes in performance level and readiness index 1. FIG. 5b shows how the on-going workout load effect on readiness index 2 preventing overload when the user has starting with heavy load. The final recovery index can be determined either on the basis of relationship shown in FIG. 5a, or by combining the FIGS. 5a and 5b or the ratio by combining the two images and by adding the recovery time which is remaining from previous exercise.

Readiness index can calculated with the formula:

$$\text{Readiness index}=A*\text{recovery time left}+B*\text{readiness index1}+C*\text{readiness index2}$$

Example: coefficients A=−1[1/h]; B=4 and C=−4.
Recovery time left=10 h; VO2max change=5 ml/kg/min;
Current workout 7 ml/kg/min, Readiness index1=5; Readiness index2=2, wherein
Readiness index=−1*10+4*5+(−4)*2=2

In this example the new exercise started, when there was still recovery time 10 h, but fitness level (performance level) was increased and workout was light (training effect was low, TE=2).

Thus, when Readiness index is used for recovery check feedback, the positive results would yield "Go for it!"

In case performance level) was decreased 5 ml/kg/min, then the formula gives −38 meaning the Readiness index being −38 and the feedback could be "Overload! Rest! High body loads. Recovery time 48 h"

The empiric formula has been built so that when readiness index is getting a positive value, the person is ready for the exercise.

An example of how instant performance level effect on feedback about readiness to exercise is shown in FIG. 7. User is warned not being ready to exercise e.g. if the earlier value is low and instant performance level is not improving. The better earlier value, the more likely the user is advised to exercise, even the instant performance level keeps showing the same level.

3) Automatic Personalization

Readiness index calculation learns from the person's history recovery needs and automatically adapts to their own level. Readiness index calculation takes into account the long-term changes in performance levels and physical activity. For example, if the person does a hard workout but the performance level is, however, higher than in the past, the readiness could be relatively better than the training effect based readiness. In turn, if person does some easy workout but the performance level is going down (because of acute performance level decrease due to for example tiredness or illness), readiness index be lower than in some previously performed a hard training session which is done during increasing performance level. See an example of automatic personalization in FIG. 8.

4) Training Advisor

When readiness index is defined, it can be utilized for various applications and the basis of feedback. These kinds of applications are for example recovery time, exercise guidance and feedback about readiness to exercise.

The timing of supercompensation and the recovery needs is an individual and it will greatly be affected of the acute situations, such as training, stress, eating and sleeping. The real recovery is unknown until the recovery has taken place. The best and the only indisputable measure of readiness to exercise is the change of performance.

FIGS. 13a, 13b and 13c show an example of how the following of current workout performance level development can be used to provide feedback about readiness to exercise and recovery time, and give exercise guidance. Feedback can be given based on the absolute or relative change in fitness level. Feedback is based on the change in performance level according to exercise. When the performance level has increased or decreased over predetermined value, the feedback is given. Feedback can also be given, if the user's performance level will remain unchanged. Feedback about performance level change takes into account the current exercise load (for example EPOC and TE), exercise duration, training history and fitness level change during previous exercises. Feedback can be given based on current exercise performance level change and also comparing it with the previous exercises' performance level changes.

In FIG. 13a, the performance level increases during the exercise and user do easy/recovering exercise. The device tells to the user that the exercise was light and no recovery is required. FIG. 13b shows an example about heavy exercise. In the beginning of the exercise performance level increases but heavy exercise decreases performance level and causing improving workout. In FIG. 13c the user does the same exercise as in FIG. 13b but in the beginning of the exercise readiness to exercise is in low level and performance level decreases. Despite this the user continues heavy exercise and the exercise causes an acute overload situation to the user. The device tells the user that the recovery is still in progress, user could be better to take it easy and because the exercise caused overload the recovery need is high.

An integral part of the present invention is to give feedback to the user by scaling the recovery time for a meaningful interpretation, capacity to respond to the new exercise and training feedback. Feedback can be given during or after exercise visually, verbally or auditory. See on example in FIG. 10.

FIG. 9 shows another software implementation of the method for a wristop or other device. The calculation of Readiness index uses input parameters: instant Recovery time left, instant achieved training effect (TE), current and previous performance level (maxMET and History maxMET), minutes of valid data for maxMET (reliability). The difference between current and previous performance level is calculated in module 52. Using other input parameters and said change (ΔmaxMET) instant Readiness index is calculated in module 54 into the register 56. The execution is lead then condition modules 58, 60, 62. According to condition 58 if the workout ends, the final Readiness index is the last instant Readiness Index, otherwise the condition 60 "Warm-up Readiness check already completed?" is executed.

If this check was already completed, the execution returns to module 54 for recalculating Readiness Index otherwise duration of valid data is check by condition 62 "Minutes valid data for maxMETt>2 min?". In a positive result (yes) Readiness Index is taken as it was at warm-up and the execution goes back to module 54, otherwise (result='No') the execution returns directly to module 54 for said recalculating.

Thus, the user is guided as soon as possible by recovery check result until after workout new check is made.

In addition to the absolute readiness index the method provides also verbal feedback. See an example method in FIG. 11.

Training advisor can include also training recommendations during or after exercise. The feedback may also relate to the target, which can be a longer-term target or goal of the workout. The long-term goal may be a target time for a specific marathon. The objective of the exercise can be for example a "heavy exercise" or "recovery exercise" and the device gives feedback about the success of exercise towards to goal. For example, if the aim is the recovery exercise and performance level seems to decrease during exercise, the device notice to the user about that and give the necessary training instructions. Recommendation can be given by numeric or verbal. An example of training advisor's interpretation and training recommendation. Green: "Full recovery", "Go for it", Full charge. Red: "Ease up a bit", Drained.

The system and method according to the invention can be applied in many kinds of device, e.g. a wrist top device with a heart-rate transmitter, generally in a system having CPU, memory and software therein is needed. This kind of hardware assembly was presented in document WO2007/099206A1 (Coach). However, new software is needed for implementing performance level (FIG. 4a), Readiness index (FIG. 9) and the recovery assessment described above. According to FIG. 12, in a typical application (e.g., wristop device) the implementation comprises an assembly built around a central processing unit (CPU) 32. A bus 36 transmits data between the central unit 32 and the other units. The input unit 31, ROM memory 31.1, RAM memory 31.2, keypad 18, PC connection 37, and output unit 34 are connected to the bus.

The system main comprise a data logger which can be connected to cloud service. The data logger measure physiological response and/or external workload.

The heart rate sensor 12 and some sensor 30 registering external output are connected to the input unit 31, which handles the sensor's data traffic to the bus 36. Optionally, the PC is connected to a PC connection 37. The output device, for example a display 15, is connected to the output unit 34. In some embodiments, voice feedback is created with the aid of a voice synthesizer and a loudspeaker 35, instead or, or in addition to the feedback on the display. The sensor 30 measuring external work can, in fact, comprise a group of sensors, which are used together to define the external work done by the user.

More specifically the system presented in FIG. 12 has following minimum parts for determining body's readiness to respond to physical exercise and provide feedback to a user. There are

- a heart rate sensor (32) configured to measure the heartbeat of the person, the heart rate signal being representative of the heartbeat of the user;
- at least one sensor (30) to measure an external workload during an exercise, and
- a data processing unit (32) operably coupled to the said sensors (12, 30), a memory (31.1, 31.2) operably coupled to the data processing unit (32),
- the memory configured to save background information of a user, said background data including an earlier performance level.

The data processing unit (32) is configured

- to determine an instant performance level of the user by a relation of measured exercise intensity and external workload;
- to calculate frequently an instant performance level of the user by a relation of measured exercise intensity and measured external workload;
- to compare the earlier performance level to the calculated instant performance level;
- to calculate a readiness index according to the said comparison, background information and training history; and
- to provide feedback according to the calculated readiness index.

All of the default values of the optional parameters are preferably stored in a ROM memory, or more specifically, e.g. in an EEPROM (Electrically Erasable Programmable Read-Only Memory) memory.

For example, the user's "external" data:
sex: man, age 35 years, weight 75 kg, height 180 cm.
User's more demanding data:
fitness level (VO2max):40 ml/kg/min; Activity class 4.

In a web service, the default values of the parameters are preferably recorded in self-service software.

In these embodiments, it would be as such also possible to use some other method than that described above as a fitness test. However, the fitness test according to the invention provides several advantages in terms of automatic updating. It can be completely integrated in many standard-model wristop devices and demands substantially fewer calculation stages than the method according to the WO publication.

The invention claimed is:

1. A method for determining a body's readiness to respond to physical exercise, using a performance check, and providing feedback to a user, wherein the user starts to perform an exercise and where an earlier performance level is determined in an earlier exercise before the performance check and stored in a memory operably coupled to a data processing unit, the method comprising:
   - measuring, by a heart rate sensor, heart rate and determining, by the data processing unit, exercise intensity from measured heart rate, and simultaneously determining the external workload by measuring or inputting manually,
   - determining, by the date processing unit, an instant performance level of the user by a relation of exercise intensity and determined external workload, the exercise intensity being determined by measured heart rate,
   - comparing, by the data processing unit, the earlier performance level stored in the memory, to the instant performance level,
   - determining, by the data processing unit, a readiness index according to the said comparison and, optionally with background information and training history, providing feedback according to the determined readiness index.

2. The method according to claim 1, wherein the earlier exercise precedes immediately the said exercise regarding determining the body's readiness, whereby background information data and the earlier performance level are determined by the earlier exercise.

3. The method according to claim 1, wherein the training history includes information from the current performed exercise, which is used when the readiness index is determined.

4. The method according to claim 3, wherein the readiness index is adapted by history data containing a training effect of the performed exercise.

5. The method according to claim 4, wherein the readiness index is adapted by a recovery time, which is remaining from previous exercise determined after the exercise is fully performed.

6. The method according to claim 1, wherein the exercise intensity and the external workload are measured frequently by respective sensors.

7. The method according to claim 6, wherein the instant performance level is calculated statistically from a plurality of sequential instant values, each of which is weighted by reliability according to preset criterion.

8. The method according to claim 7, wherein the input values are filtered by preset criteria.

9. The method according to claim 1, wherein the exercise belongs to a group consisting: walking, biking, running.

10. The method according to claim 1, wherein the feedback is exercise feedback.

11. The method according to claim 9, wherein the feedback is provided towards a target.

12. The method according to claim 9, wherein the user is advised by the feedback at least with one of the following options:
   - to continue training normally if the determined readiness index indicates an improved performance level or being in a previous level, to ease up training if the determined readiness index indicates a decreased performance level.

13. The method according to claim 1, wherein a reliability of a value of the instant performance level is detected and each value with a low reliability is automatically excluded.

14. The method according to claim 1, wherein an exercise modality is detected.

15. The method according to claim 1, wherein the start of the performing of the exercise is detected automatically.

16. The method according to claim 1, wherein an indication of fatigue is determined based on the change of the performance level using preset criteria.

17. A system for determining a body's readiness to respond to physical exercise and provide feedback to a user, the system comprising:
- a heart rate sensor configured to measure the heartbeat of the person, the heart rate signal being representative of the heartbeat of the user;
- at least one sensor to measure an external workload during an exercise, and
- a data processing unit operably coupled to the said sensors, a memory operably coupled to the data processing unit,
- the memory configured to save background information of a user, said background data including an earlier performance level; wherein the data processing unit is configured to:
  - determine an instant performance level of the user by a relation of measured exercise intensity and external workload;
  - calculate frequently an instant performance level of the user by a relation of measured exercise intensity and measured external workload;
  - compare the earlier performance level to the calculated instant performance level;
  - calculate a readiness index according to the said comparison, background information and training history; and
  - provide feedback according to the calculated readiness index.

18. The system according to claim 17, wherein the system is implemented in one of the following: a heart rate monitor, a fitness device, a mobile phone, a PDA device, a wristop computer or personal computer having software for implementing said software means and hardware for execution of the software and giving feedback.

19. The system according to claim 17, wherein the external workload is measured by position tracking.

* * * * *

UNITED STATES PATENT AND TRADEMARK OFFICE
CERTIFICATE OF CORRECTION

PATENT NO. : 10,238,915 B2
APPLICATION NO. : 14/912242
DATED : March 26, 2019
INVENTOR(S) : Aki Pulkkinen, Sami Saalasti and Kaisa Hämäläinen It is certified that error appears in the above-identified patent and that said Letters Patent is hereby corrected as shown below:

In the Specification

Column 2,
At Line 53, "external workout" should be changed to -- external workload --;
At Lines 55-57, please delete "an instant performance level of the user is determined by a relation of measured exercise intensity and determined external workload,".

Column 7,
At Line 28, "After start internal and" should be changed to -- After start internal response (R-R-intervals) and --;
At Line 29, "external exercise workout" should be changed to -- external exercise workload --;
At Line 30, "External workout" should be changed to -- External workload --;
At Line 35, "maxMET = maxMET(HR, maxHR, external exercise workout)." should be changed to -- maxMET = maxMET(HR, maxHR, external exercise workload). --.

Signed and Sealed this
First Day of October, 2019

Andrei Iancu
*Director of the United States Patent and Trademark Office*